United States Patent
Robinson

[11] 4,011,750
[45] Mar. 15, 1977

[54] METHOD AND APPARATUS FOR ULTRASONIC EXAMINATION OF OBJECTS

[75] Inventor: David Errol Robinson, Avalon Beach, Australia

[73] Assignee: The Commonwealth of Australia care of the Secretary Department of Health, Australian Capitol Territory, Australia

[22] Filed: June 30, 1975

[21] Appl. No.: 591,311

Related U.S. Application Data

[63] Continuation-in-part of Ser. No. 367,628, June 6, 1973, abandoned.

[52] U.S. Cl. .................................................. 73/67.7
[51] Int. Cl.² ............................................. G01N 29/04
[58] Field of Search ........ 73/67.7, 71.5 US, 67.8 R, 73/67.8 S, 67.9; 340/1 R, 8 R, 8 L, 10

[56] References Cited
UNITED STATES PATENTS

| | | | |
|---|---|---|---|
| 3,066,525 | 12/1962 | Harris | 73/67.8 |
| 3,090,030 | 5/1963 | Schuck | 340/1 R |
| 3,136,381 | 6/1964 | Anderson | 340/10 |
| 3,299,694 | 1/1967 | Dickenson | 73/67.7 X |
| 3,327,286 | 6/1967 | Dorr et al. | 340/8 R |
| 3,332,278 | 7/1967 | Wood et al. | 73/67.7 |
| 3,457,543 | 7/1969 | Akervold et al. | 340/10 |
| 3,513,439 | 5/1970 | Egli | 340/10 |
| 3,616,682 | 11/1971 | Golis et al. | 73/67.7 |

*Primary Examiner*—Richard C. Queisser
*Assistant Examiner*—John P. Beauchamp

[57] ABSTRACT

Apparatus for the ultrasonic examination of an object comprising a transmitter for transmitting pulses of ultrasonic energy into the object and a receiver for receiving echoes of the pulses of ultrasonic energy reflected by acoustic impedance discontinuities within the object, wherein the transmitter comprises a central transducer adapted to transmit pulses along a single axis and a plurality of annular transducers positioned concentrically with the axis of the central transducer. The receiver comprises the central transducer, the central transducer being adapted to receive echoes of pulses transmitted into the object by each of the central transducer and the annular transducers which are reflected along the single axis thereof, the apparatus further comprising circuitry for analyzing the received echoes of pulses transmitted by each of the central transducer and annular transducers to extract velocity, scattering, and multiple reflection information.

18 Claims, 9 Drawing Figures

METHOD AND APPARATUS FOR ULTRASONIC EXAMINATION OF OBJECTS

CROSS REFERENCE TO RELATED APPLICATIONS

This application is a Continuation-In-Part application of U.S. Pat. application Ser. No. 367,628, filed June 6, 1973 now abandoned.

BACKGROUND OF THE INVENTION

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilising this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may consitutute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propogation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceeding of the Institution of Radio and Electronics Engineers Australia, Vol. 31, No. 11, pages 385–392, Nov., 1970: "The Application of Ultrasound in Medical Diagnosis." As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

This known system suffers from several disadvantages due to ambiguity in the received echo formation:- i. The magnitude of the echo received is dependent on the reflectivity of the surface, its angulation with the beam and the scattering properties of the surface. When the reflector is sharply inclined to the beam no echo is returned.

ii. An echo at a particular range may be produced by a direct two-way travel in which case the indicated location of the reflecting surface is correct. However the pulse may be reflected several times within the examined object giving rise to false indication of a reflecting surface at a range at which none exists.

iii. Errors in the indicated positions of reflecting surfaces in the examined object due to local changes in velocity of propagation of the ultrasonic energy through the object are not detectable, nor is the velocity of propagation measurable.

It is a primary object of the present invention to provide an improved apparatus and method for the ultrasonic echoscopic examination of objects whereby more reliable and more useful information may be obtained concerning the examined objects. The improvement lies in a greatly extended capacity of the information acquisition and processing system which gives rise to one line of ultrasonic data on a two-dimensional display. This line with increased information may then be used in the same way as a simple pulse echo signal line to provide a two dimensional picture according to the current art as explained above.

According to this invention, there is provided apparatus for the ultrasonic examination of an object comprising means for transmitting pulses of ultrasonic energy into the object and means for receiving echoes of said pulses of ultrasonic energy reflected by acoustic impedance discontinuities within the object, wherein: said means for transmitting pulses comprises a central transducer adapted to transmit pulses along a single axis and a plurality of annular transducers positioned concentrically with said axis of the central transducer, and said means for receiving echoes comprises said central transducer, the central transducer being adapted to receive echoes of pulses transmitted into the object by each of said central transducer and said annular transducers which are reflected along said single axis thereof, said apparatus further comprising means for separately storing and then subsequently analysing said received echoes of pulses transmitted by each of said central transducer and said annular transducer to extract velocity, scattering, and multiple reflection information.

In an alternative embodiment, this invention provides apparatus for the ultrasonic examination of an object comprising means for transmitting pulses of ultrasonic energy into the object and means for receiving echoes of said pulses of ultrasonic energy reflected by acoustic impedance discontinuities within the object, wherein: said means for transmitting pulses comprises a central transducer adapted to transmit pulses along a single axis, and said means for receiving echoes comprises said central transducer and a plurality of annular transducers positioned concentrically with said axis of the central transducer, each of said central transducer and said plurality of transducers being adapted to receive reflected echoes of pulses transmitted into the object by said central transducer along said single axis thereof, said apparatus further comprising means for separately storing and then subsequently analyzing said received echoes of pulses transmitted by said central transducer to extract velocity, scattering, and multiple reflection information.

This invention also provides a method of ultrasonic examination of an object comprising the steps of transmitting pulses of ultrasonic energy into the object and receiving echoes of said pulses of ultrasonic energy reflected by acoustic impedance discontinuities within the object, wherein: said pulses are transmitted along a single axis by a central transducer and by a plurality of annular transducers positioned concentrically with said axis of the central transducer, and echoes of pulses transmitted into the object by each of said central transducer and said annular transducers reflected along said single axis are received by said central transducer, said method including separately storing and then subsequently analyzing said received echoes of pulses transmitted by each of said central transducer and said annular transducers to extract velocity, scattering and multiple reflection information.

In yet another embodiment, the invention provides a method of ultrasonic examination of an object comprising the steps of transmitting pulses of ultrasonic energy into the object and receiving echoes of said pulses of ultrasonic energy reflected by acoustic impedance discontinuities within the object, wherein: said pulses are transmitted along a single axis by a central transducer, and reflected echoes of pulses transmitted into the object by said central transducer along said single axis thereof are received by each of said central transducer and a plurality of annular transducers positioned concentrically with said axis of the central transducer, said method including separately storing and then subsequently analyzing said received echoes of pulses transmitted by said central transducer to extract velocity, scattering and multiple reflection information.

It will be appreciated from the above that in use of either embodiment of the apparatus of the present invention, a set of paths is generated along which the pulses are transmitted and echoes received. This system is thus quite different to an axial system using a single line of sight along the axis of symmetry and as the echoes received along each path in accordance with the present invention are kept separate for the purpose of analysis, in this respect the present system differs from annular array systems in the current art.

In a preferred aspect of the invention, the active area of the central transducer is a disc with focusing properties and the beam axis of the transducer lies along a line through the centre of the disc at right angles to it's surface. Methods of achieving focusing properties are well known. For instance a simple geometrical focus can be obtained as described in the scientific literature by G. Kossoff "Design of Narrow Beam Width Transducers" J. Acoust. Soc. Amer., 35, 6 (June 1963); 905–912. Alternatively an annular geometry may be used as described in U.S. Pat. No. 3,327,286. The active areas of the annular transducers are preferably arranged to be in the shape of thin annular rings whose axes lie along the same line as the axis of the central transducer. The diameters of the annular transducers are preferably of substantially larger diameter than the diameter of the disc of the central transducer and the width of each of the annular transducer is preferably small compared with the diameter of the disc of the central transducer. Typically, the diameters of the annular transducers are up to the same order of size as the distance from the transducer face to the examined object. By way of example, there may be from four to ten annular transducers in the apparatus.

The annular transducers may lie in the same plane as the central transducer, or they may be positioned to lie on the surface of a cone, sphere or other solid of revolution whose axis is the axis of the central transducer. In addition, each of the annular transducers may consist of a single element or alternatively it may be broken up into a number of separate segmental elements.

The central and annular transducers may consist of any type of electromechanical transducer.

In operation of the apparatus of the present invention in which the central transducer acts as the receiver, for one cycle of operation each transmitting transducer is pulsed in turn. Between pulses the receiver is activated and echoes received from along the receiver axis. The time delays of echoes received from each annular transducer are corrected to correspond to known distances along the receiver axis. A similar mode of operation is utilized where the central transducer acts as the transmitter, although if desired, echoes of a single pulse may be simultaneously received by the plurality of annular transducers. In either case, the sets of echoes corresponding to each beam path are kept separate for subsequent processing and analysis.

Processing of the information obtained in accordance with the present invention takes advantage of the fact that the ultrasound travels in a number of discreet paths which are not along the axis of the system and may be implemented by analogue or digital techniques and may consist of a number of steps:

i. By taking the echoes which are stored as a function of time delay and correcting them to account for the different path lengths travelled by the signals from the different transducers and for the velocity of propagation in the medium, a signal consisting of echoes as a function of distance along the axis is obtained. Echoes received from the same interface along different paths can then be directly compared, added, or otherwise combined.

ii. By adding echoes at common distances along the axis for all transmitted pulses in a cycle, inclined reflecting surfaces are displayed as echo indications as well as reflecting surfaces at right angles.

iii. By comparision of echo magnitude at a common distance for all pulses in a cycle, the scattering properties of a reflecting surface may be determined. Thus a measure of the reflectance and the roughness of the reflecting surface are obtained.

iv. By analysis of the difference in indicated distance between echoes which are apparently from the same reflecting surface of presence of multiple reflection artifacts is revealed.

v. By comparison of the distance difference and consideration of the outlines of anatomical structure an estimate of the velocity of propagation in areas of the medium may be obtained.

The invention is illustrated in the accompanying drawings in which.

Figure 1:
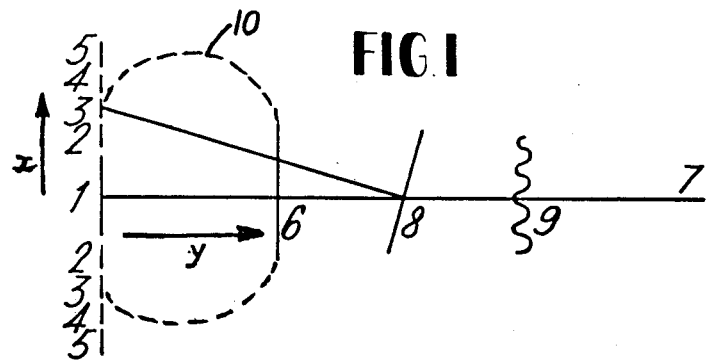
FIG. 1 is a schematic representation of apparatus in accordance with the present invention.
Figure 2:
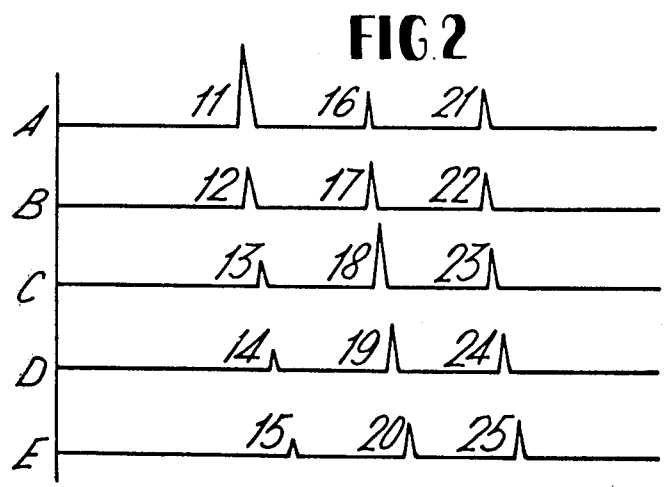
FIG. 2 is a diagrammatic representation of typical echo patterns receiving using the apparatus of the invention.

In FIG. 1 the annular transmitting transducers consist of an axially symmetrical set of rings shown in cross-section with disc 1 representing the central element and receiving transducer, and annular rings 2 to 5 being used as off axis transmitters. The scanned object includes, by way of example, an interface 6 at right angles to the beam axis 7 with a smooth inclined interface 8 and a rough (scattering) interface 9. The resultant echo patterns are illustrated in FIG. 2 in which A to E represent the received signals at the receiving transducer 1 for transmitted pulses from transducers 1 to 5 respectively. The echoes 11 to 15 originate at interface 6, echoes 16 to 20 originate at interface 8, and echoes 21 to 25 at interface 9. With the distance from the beam axis to an annular transducer element called $x$ and the distance from the transducer face to the reflector called $y$ as shown in FIG. 1, the total ray path called $d$ to be traversed by an ultrasonic pulse used according to the teaching of the invention is given by the relationship $$d = \sqrt{x^2 + y^2} + y \qquad \text{Equation 1.}$$

whence the value of $y$, the depth to an interface is given by $$y = \frac{d^2 - x^2}{2d} \qquad \text{Equation 2.}$$

If the velocity of propagation is constant and of amount $c$, the total path length $d$ is equal to $c \times t$ where $t$ is the travel time of the pulse. Thus the depth to an interface is given by $$y = \frac{c^2 t^2 - x^2}{2ct} \qquad \text{Equation 3.}$$

Figure 3:
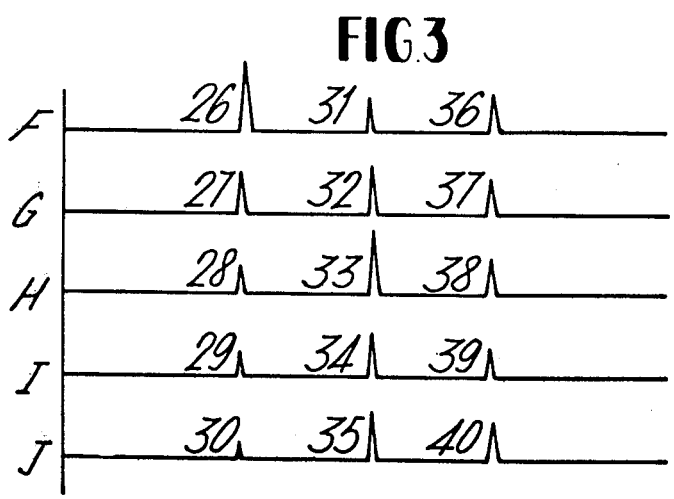
FIG. 3 is a diagrammatic representation of the echo patterns of FIG. 2 which have been time-corrected.

It is clear from this relationship that echoes from a contant interface occur at later and later times as the value of $x$ increases, that is from wider and wider annular rings. It is also clear that assuming a particular value of velocity $c$ and by applying equation 3, the echoes may first be corrected for the difference in travel time from the various transmitters and the time corrected echoes are shown in FIG. 3 in which signals F to J correspond to corrected versions of the signals A to E respectively. Thus, echoes 26 to 30, 31 to 35 and 36 to 40 correspond to corrected versions of echoes 11 to 15, 16 to 20 and 21 to 25 respectively. It is clear that echo 26 is the largest of its group and the amplitude drops quickly from 26 to 30 indicating that the echo size varies rapidly with angle and the reflector is a smooth interface at right angles to the beam. Echo 33 is the largest of its group and the amplitude drops less rapidly indicating an inclined interface with a small roughness. Echoes 36 to 40 are all of similar amplitude indicating that the echo size is independent of angle and the reflector is a rough scattering interface with no mirror-like reflecting properties. The signal combination means 82 can readily be adapted to provide a composite signal to indicate the position of all rough interfaces, or all smooth interfaces resulting from the comparisons detailed above as selected by the operator using operator input means 84. If an in-appropriate value for $c$ was chosen for use in equation 3, then the time-corrected echoes in signals F – J would not superimpose. In the case of an unknown $c$ it is possible to generate a number of versions of signals F–J with different trial values and compare the results to see which value of $c$ gives the best correspondence between signals F–J. In the case of a medium in which the velocity varies for example in FIG. 1 where region 10 may have a different velocity than the remainder of the medium, the process of generating results with trial values is carried out only for echoes 11–15 to obtain the value of $c$ between the transducers face and interface 6. The process is then repeated for echoes 16–20 to determine the velocity of propagation between interfaces 6 and 8. This system can be extended in a straight forward way to analyse the velocity in regions which are not symmetrical about the axis of the system.

Alternatively in the case of an unknown value for the velocity $c$, it is possible to ascertain this value by comparison of delays in reflected echoes to known geometrical points within the objects, again utilising the above equations.

Figure 4:
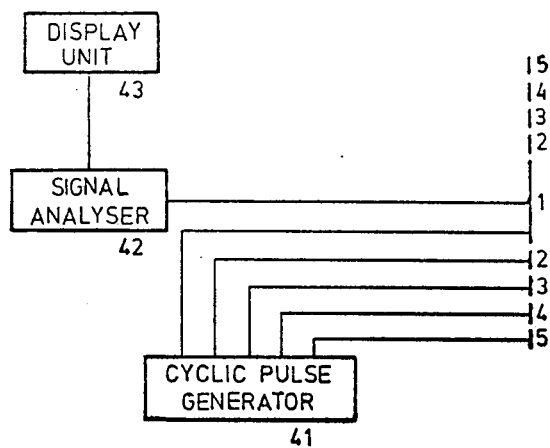
FIG. 4 is a block diagram of the apparatus for ultrasonic examination of an object showing the central transducer being used as the sole receiving element.
Figure 5:
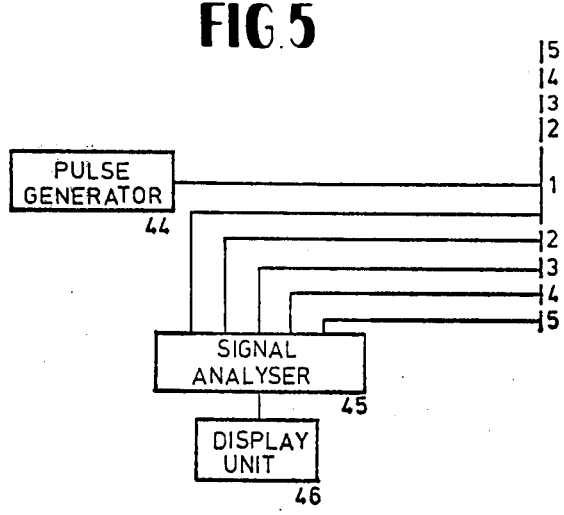
FIG. 5 is a block diagram of the apparatus for ultrasonic examination of an object showing the center transducer as the sole transmitting element.

FIGS. 4 and 5 illustrate the manner in which a receiver and transmitter are generally connected to the transducer array. FIG. 4 shows the arrangement wherein the central disc 1 is used as the sole receiving element, while transducers 1–5 are utilized as transmitting elements. FIG. 5 shows the inverse situation in which central disc 1 is used as the sole transmitting element, and transducers 1–5 are used as receiving elements. In both arrangements of the transmitter and receiver, the receiver includes means for analyzing the received signals to extract velocity, scattering, and multiple reflection information and means to display the received and analysed information.

In use of the apparatus illustrated in FIG. 4, pulse generator 41 generates a pulse by well known means to excite element 1. Echoes are received along the axis and stored by signal analyser 42. Pulse generator 41 then excites element 2 and its echoes are received along the axis by element 1 and stored. When all transmitting elements have been excited and the echoes received, the echoes are compared as previously described, the required information extracted and then displayed using well known techniques on display unit 43.

In FIG. 5, central element 1 is pulsed by pulse generator 44. Echoes are received simultaneously at elements 1 to 5 and stored separately in signal analyser 45, analysed as before and displayed on display unit 46.

Figure 6:
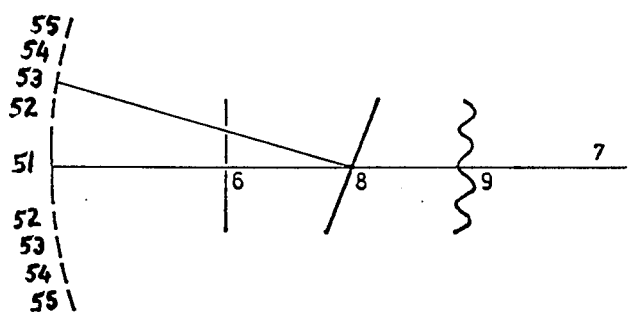
FIG. 6 shows an alternative arrangement of the transducers in accordance with one embodiment of the invention.

In certain embodiments, it may be advantageous to change the shape of the transducer array to reduce the time differences between various signal path lengths involved. This may be achieved by placing the elements of the transducer array on a surface of revolution such as a cone or a sphere as shown for example in FIG. 6 in which elements 51–55 lie on the surface of a solid of revolution but play the same role as elements 1 to 5 in the previous figures. Appropriate changes are necessarily applied to the delay times of signals A to E in FIG. 2.

Figure 7:
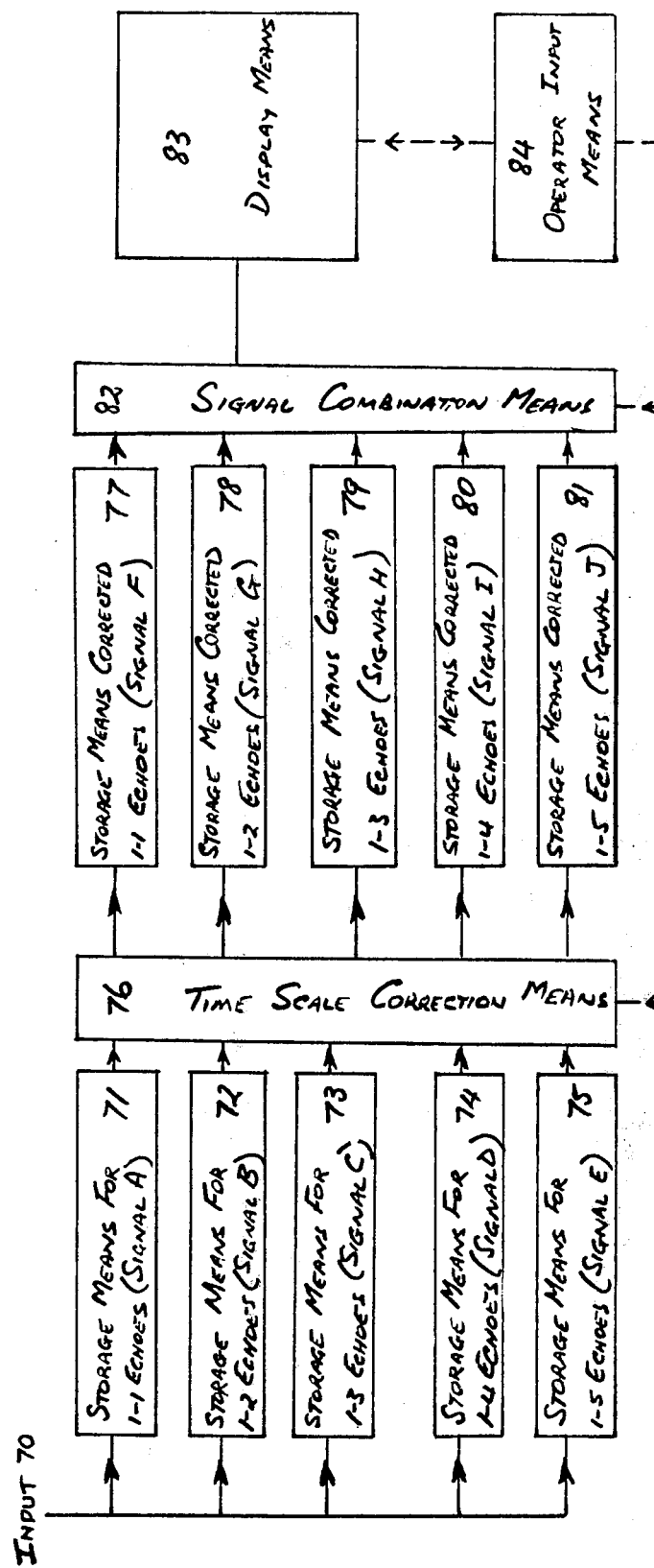
FIG. 7 is a block diagram of the apparatus for analysis of the received echoes. This processing scheme is applicable for both arrangements for receiving and transmitting as shown in FIG. 4 and FIG. 5.

FIG. 7 shows one embodiment of analyser 42 in FIG. 4 or 45 in FIG. 5. The input 70 to the analyser from the receiving transducer or transducers is appropriately fed to a plurality of storage devices 71–75. For example, the echo signal obtained from the beam path from transducer 1 back to transducer 1 is stored as signal A of FIG. 2 in storage means 71, the echo between transducer 1 and transducer 2 is stored as signal B of FIG. 2 in storage means 72, and so on. Time scale correction means 76 performs the correction given by Equation 3 above which relates the time $t$ with the interface depth $y$ according to the value of $x$. For signal A where $x$ is zero the correction is simply a linear relationship between $y$ and $t$ to obtain corrected signal F in FIG. 3 which is stored in storage means 77. For signal B the correction involves a shift of echoes along the horizontal axis to obtain corrected signal G which is stored in storage means 78, and so on. Signal combination means 82 may be operated in a number of modes depending on the process required. In one mode it would operate as a switch to select only one signal from the signals F to J for display. In an alternative mode it would operate as an adder to add together a selected combination or all of signals F to J, so as to combine all echoes from constant apparent depth in a composite display. In another mode of operation it would perform the mathematical process of cross correlation between selected signals to determine the degree of similarity between them. Display means 83 is a standard display as used in the current art and is preferably a cathode ray tube. Operator input means 84 is provided to allow the operator to select the mode of operation of signal combination means 82 and set the parameters for time scale correction means 76. The apparatus of FIG. 7 has been described and drawn in the form of a flow chart suitable for writing a digital computer programme. In this embodiment, the storage means 71–75 and 77–81 are memory locations, the time scale correction means 76 and signal combination means 82 are computer programmes and operator input means 84 is a keyboard or other standard interactive terminal. To those skilled in the art, it will be clear that the processing described can be implemented using an analog system with a multichannel type recorder for storage means 71–75 and 77–81 and a system of moveable playback heads for time scale correction means 76. The signal combination means 82 can then be an electronic adder, a switch or a commercially available cross correlator instrument depending on the mode selected by the operator. The processing system can like-wise be implemented in an all-digital system with shift-registers for storage means 71–75 and 77–81, with variable rate clocking for time scale correction 76 and switches, digital adder, and correlator instrument for signal combination means 82.

Figure 8:
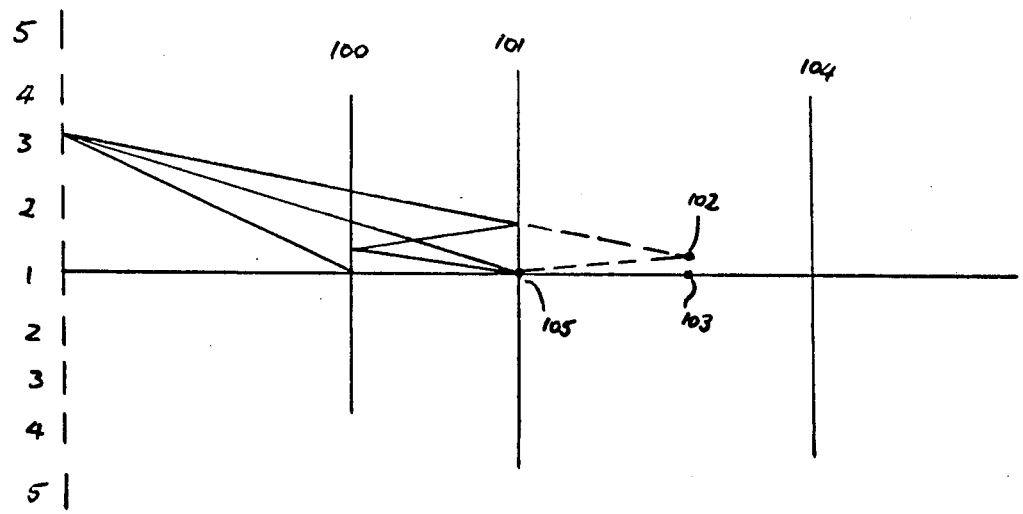
FIG. 8 is a schematic representation of apparatus to describe the operation of the processing system to identify artifact echoes.

FIG. 8 shows a slightly different structure than FIG. 1 of the examined medium to demonstrate the method of identifying multiple reflection artifact echoes, the existence of which is well known in the art. For the purposes of illustration, this figure includes three interfaces 100, 101 and 104. True echoes are received at correct time delays from each interface. In addition, for the axial path from transducer 1 to transducer 1, an echo is received which has travelled from transducer 1 to interface 101, to interface 100, back to interface 101 and thence to transducer 1, the echo appearing to have come from point 103. Similarly, in the inclined ray path between transducer 1 and transducer 3, an additional echo occurs which appears to come from point 102. Clearly, the distance from transducer 3 to point 102 to axis point 105 on interface 101 to transducer 1 is a smaller distance than the distance from transducer 3 to point 103 to transducer 1, and thus the artifact echo seems to come from a closer interface when viewed from a wider annular ring.

Figure 9:
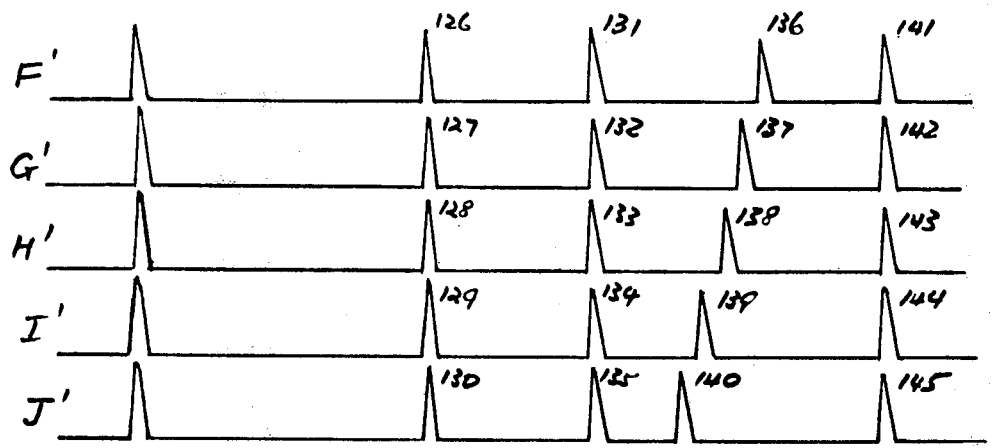
FIG. 9 is a diagrammatic representation of time-corrected echo patterns when artifact echoes are encountered.

FIG. 9 shows a set of time corrected echoes similar to those of FIG. 3 but corresponding to the situation of FIG. 8. Echoes 126–130 come from interface 100, echoes 131–135 from interface 101, echoes 141–145 from interface 104 and echoes 136–140 are from multiple reflection between interfaces 100 and 101. As can be seen, the artifact echoes 136–140 do not align, whereas all other corresponding echoes do. When the traces F'–J' are combined for instance by additions, the real echoes superimpose and reinforce, while the artifact echoes do not and their relative size is reduced.

From the foregoing description it will therefore be appreciated that the present invention enables more reliable and useful information to be obtained in the ultrasonic examination of objects. In particular the invention enables the angular reflecting properties of reflectors to be investigated, the velocity of propagation in regions within the medium to be determined and artifact echoes to be identified and suppressed. The present invention when combined with the well-known two-dimensional visualisation technique has certain other incidental advantages. For instance the greater tolerance to angulation of reflectors reduces the need for the common technique of compound scanning and thus reduces the time necessary to form a picture. It is a logical extension of the invention to restrict its operation to a single plane by providing only small segments of the annular rings. The transducer array then becomes a linear one. In this extension the application of the invention to measurement of velocity in isolated regions in the medium when used in conjunction with two-dimensional visualisation is considerably simplified.

While the invention has been described with reference to preferred embodiments, it will be generally understood by those skilled in the art that various changes may be made and equivalents may be substituted for elements thereof without departing from the true spirit and scope of the invention.

I claim:

1. Apparatus for the ultrasonic examination of an object comprising means for transmitting pulses of ultrasonic energy into the object and means for receiving echoes of said pulses of ultrasonic energy reflected by acoustic impedance discontinuities within the object, wherein:

said means for transmitting pulses comprises a central transducer adapted to transmit pulses along a single axis and a plurality of annular transducers positioned concentrically with said axis of the central transducer, the active area of said central transducer comprising a transducer disc of the type having focusing properties, the beam axis of the transducer disc lying along a line through the center of the disc at right angles to the surface thereof, and said means for receiving echoes comprises said central transducer, the central transducer being adapted to receive echoes of pulses transmitted into the object by each of said central transducer and said annular transducers which are reflected along said single axis thereof, said apparatus further comprising means for analysing said received echoes of pulses transmitted by each of said central transducer and said annular transducers to extract velocity, scattering, and multiple reflection information.

2. Apparatus as claimed in claim 1, characterized in that the active areas of the annular transducers comprise annular rings whose axes of symmetry lie along the same line as the axis of the central transducer.

3. Apparatus as claimed in claim 2, characterized in that the diameters of the annular rings are substantially larger than the diameter of the disc of the central transducer.

4. Apparatus as claimed in claim 2, characterized in that the width of the annular rings is small compared with the diameter of the disc of the central transducer.

5. Apparatus as claimed in claim 1, characterized in that the annular transducers are positioned to lie in the same plane as the central transducer.

6. Apparatus as claimed in claim 1, characterized in that the annular transducers are positioned to lie on the surface of a solid of revolution, the axis of which is the axis of the central transducer.

7. Apparatus as claimed in claim 1, characterized in that each annular transducer comprises a single element.

8. Apparatus as claimed in claim 1, characterized in that each annular transducer comprises a plurality of separate segmental elements.

9. A method of ultrasonic examination of an object comprising the steps of transmitting pulses of ultrasonic energy into the object and receiving echoes of said pulses of ultrasonic energy reflected by acoustic impedance discontinuities within the object, wherein:

said pulses are transmitted along a single axis by a central transducer and by a plurality of annular transducers positioned concentrically with said axis of the central transducer, and echoes of pulses transmitted into the object by each of said central transducer and said annular transducers reflected along said single axis are received by said central transducer, said method including separately storing and then subsequently analyzing said received echoes of pulses transmitted by each of said central transducer and said annular transducers to extract velocity, scattering and multiple reflection information.

10. Apparatus for the ultrasonic examination of an object comprising means for transmitting pulses of ultrasonic energy into the object and means for receiving echoes of said pulses of ultrasonic energy reflected by acoustic impedance discontinuities within the object, wherein:

said means for transmitting pulses comprises a central transducer adapted to transmit pulses along a single axis, the active area of said central transducer comprising a transducer disc of the type having focusing properties, the beam axis of the transducer lying along a line through the center of the disc ar right angles to the surface thereof, and said means for receiving echoes comprises said central transducer and a plurality of annular transducers positioned concentrically with said axis of the central transducer, each of said central transducer and said plurality of transducers being adapted to receive reflected echoes of pulses transmitted into the object by said central transducer along said single axis thereof, said apparatus further comprising means for analyzing said received echoes of pulses transmitted by said central transducer to extract velocity, scattering, and multiple reflection information.

11. Apparatus as claimed in claim 10, characterized in that the active areas of the annular transducers comprise annular rings whose axes lie along the same line as the axis of the central transducer.

12. Apparatus as claimed in claim 11, characterized in that the diameters of the annular rings are substantially larger than the diameter of the disc of the central transducer.

13. Apparatus as claimed in claim 11, characterized in that the width of the annular rings is small compared with the diameter of the disc of the central transducer.

14. Apparatus as claimed in claim 10, characterized in that the annular transducers are positioned to lie in the same plane as the central transducer.

15. Apparatus as claimed in claim 10, characterized in that the annular transducers are positioned to lie on the surface of a solid of revolution, the axis of which is the axis of the central transducer.

16. Apparatus as claimed in claim 10, characterized in that each annular transducer comprises a single element.

17. Apparatus as claimed in claim 10, characterized in that each annular transducer comprises a plurality of separate segmental elements.

18. A method of ultrasonic examination of an object comprising the steps of transmitting pulses of ultrasonic energy into the object and receiving echoes of said pulses of ultrasonic energy reflected by acoustic impedance discontinuities within the object, wherein:

said pulses are transmitted along a single axis by a central transducer, and reflected echoes of pulses transmitted into the object by said central transducer along said single axis thereof are received by each of said central transducer and a plurality of annular transducers positioned concentrically with said axis of the central transducer, said method including separately storing and then subsequently analyzing said received echoes of pulses transmitted by said central transducer to extract velocity, scattering and multiple reflection information.

* * * * *